(12) United States Patent
Potsko et al.

(10) Patent No.: US 8,820,604 B2
(45) Date of Patent: Sep. 2, 2014

(54) COMBINED SEVERING AND STAPLING DEVICE

(75) Inventors: Kristina Potsko, Bristol, CT (US); D'Anna M. Welsh, Bloomfield, CT (US)

(73) Assignee: Vascularvations, Bristol, CT (US)

(*) Notice: Subject to any disclaimer, the term of this patent is extended or adjusted under 35 U.S.C. 154(b) by 94 days.

(21) Appl. No.: 13/219,775

(22) Filed: Aug. 29, 2011

(65) Prior Publication Data

US 2012/0048910 A1   Mar. 1, 2012

Related U.S. Application Data

(60) Provisional application No. 61/378,120, filed on Aug. 30, 2010.

(51) Int. Cl.
| | | |
|---|---|---|
| A61B 17/068 | (2006.01) | |
| A61B 17/072 | (2006.01) | |
| A61B 17/00 | (2006.01) | |
| A61B 17/29 | (2006.01) | |

(52) U.S. Cl.
CPC ............ *A61B 17/0686* (2013.01); *A61B 17/072* (2013.01); *A61B 17/0682* (2013.01); *A61B 17/068* (2013.01); *A61B 17/00008* (2013.01); *A61B 17/00234* (2013.01); *A61B 2017/00969* (2013.01); *A61B 2017/2911* (2013.01)
USPC .......................................... 227/175.1; 227/19

(58) Field of Classification Search
CPC ............ A61B 17/068; A61B 17/0682; A61B 17/072; A61B 17/11
USPC ............................ 227/19, 175.1, 179.1, 180.1
See application file for complete search history.

(56) References Cited

U.S. PATENT DOCUMENTS

| | | | | |
|---|---|---|---|---|
| 5,312,023 A | * | 5/1994 | Green et al. ................ | 227/175.1 |
| 5,326,013 A | * | 7/1994 | Green et al. ................ | 227/176.1 |
| 5,330,486 A | * | 7/1994 | Wilk ............................. | 606/139 |
| 5,605,272 A | * | 2/1997 | Witt et al. ................... | 227/175.2 |
| 5,725,536 A | * | 3/1998 | Oberlin et al. ................ | 606/139 |
| 5,976,159 A | * | 11/1999 | Bolduc et al. ................. | 606/142 |
| 6,010,054 A | * | 1/2000 | Johnson et al. ............ | 227/176.1 |
| 6,312,437 B1 | * | 11/2001 | Kortenbach ................... | 606/139 |
| 7,090,683 B2 | * | 8/2006 | Brock et al. ................... | 606/130 |
| 2005/0216036 A1 | * | 9/2005 | Nakao ........................... | 606/142 |
| 2006/0025766 A1 | * | 2/2006 | Heinrich et al. ............... | 606/50 |
| 2006/0064085 A1 | * | 3/2006 | Schechter et al. ............. | 606/50 |
| 2007/0175951 A1 | * | 8/2007 | Shelton et al. ............. | 227/176.1 |

\* cited by examiner

*Primary Examiner* — Brian D Nash
(74) *Attorney, Agent, or Firm* — Cantor Colburn LLP

(57) ABSTRACT

An apparatus includes grasping ends movable between an open position to a closed position and a shaft coupled to the grasping ends. The apparatus also includes a handle coupled to the shaft and configured to cause the grasping ends to move from between the open and closed positions and a stapler actuator that causes a stapling mechanism within the grasping ends to deploy one or more staples. The apparatus also includes a blade coupled to the shaft and a blade actuator that causes the blade to translate between extended and detracted positions.

4 Claims, 4 Drawing Sheets

US 8,820,604 B2

COMBINED SEVERING AND STAPLING DEVICE

BACKGROUND

The present invention relates to medical devices and, in particular, to a blood vessel harvesting device.

Many modern medical procedures require harvesting blood vessels from one part of a person's body and using the harvested vessel in another part of the same person's body. For example, in coronary artery bypass surgery a blood vessel from the person having the bypass is harvested and then used to perform the bypass. Processes where a donor and recipient of the blood vessel is typically referred to as an "autologous" procedure.

In such procedures it is common to utilize either open or endoscopic vein harvesting techniques. Both of these harvesting techniques, unfortunately, typically can cause progressive intimal hyperplasia of the harvested blood vessel due to the stretching and other manipulation of the blood vessel required to harvest the vessel. Progressive intimal hyperplasia is known to contribute to blood vessel graft failure. Such failure may occur whether the procedure is an autologous procedure or in cases where the blood vessel is harvested from a donor and provided to a recipient.

SUMMARY

According to one embodiment of the present invention, an apparatus including grasping ends movable between an open position to a closed position and a shaft coupled to the grasping ends is disclosed. The apparatus of this embodiment also includes a handle coupled to the shaft and configured to cause the grasping ends to move from between the open and closed positions and a stapler actuator that causes a stapling mechanism within the grasping ends to deploy one or more staples. The apparatus of this embodiment also includes a blade coupled to the shaft and a blade actuator that causes the blade to translate between extended and detracted positions.

Other embodiments are directed to methods of harvesting a blood a vessel. In particular, the methods may include utilizing an apparatus as described herein.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
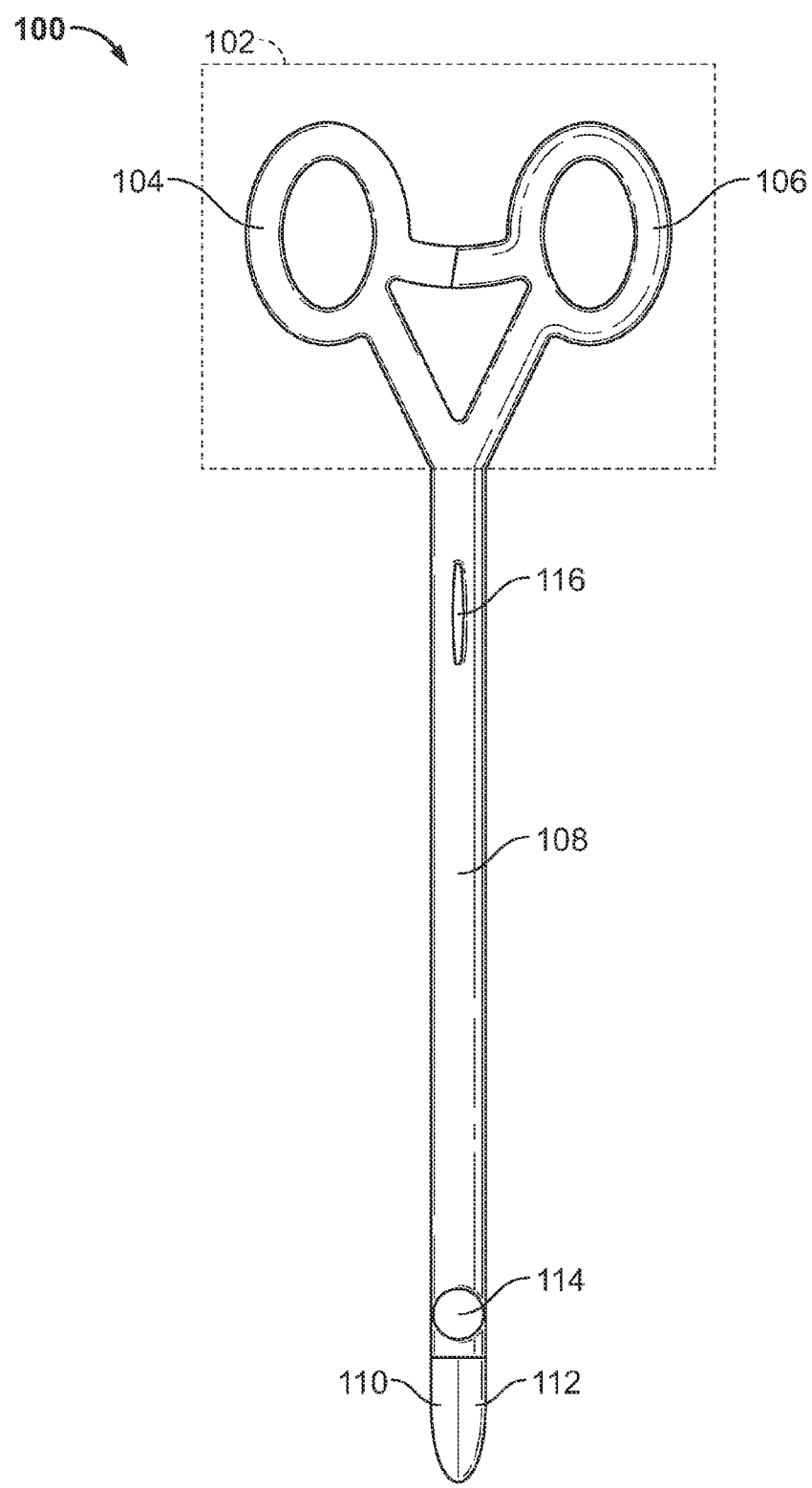
FIG. 1 shows a front plan view of an apparatus according to an embodiment of the present invention with the grasping ends in a closed position.

As discussed above, both endoscopic and open harvesting procedures can result in damage to the harvested blood vessel. In particular, in an endoscopic harvesting procedure, at the ligation site the blood vessel is typically grasped from a sub-dermal location and pulled to the surface. Such pulling can cause or increase progressive intimal hyperplasia in the blood vessel. In the case of an open procedure, the blood vessel is pulled towards a harvester. Again, this can lead to progressive intimal hyperplasia.

Accordingly, one embodiment of the present invention is directed to an apparatus that may allow for a blood vessel to be sealed and cut without pulling on the blood vessel. In particular, an embodiment of the present invention, and as shown in FIGS. 1-4, is directed to an apparatus that includes both sealing and cutting elements that may be provided to a blood vessel ligation site without requiring that the vessel be pulled to the surface. It shall be further appreciated that the apparatus shown in FIGS. 1-4 can be operated with one hand. As such, the same person operating an endoscope to locate the blood vessel can also harvest the vessel at the same time.

The apparatus 100 includes a handle portion 102. The handle portion 102 is illustrated as containing a first finger loop 104 and a second finger loop 106. It shall be understood that while the handle portion 102 is shown including finger loops 104, 106, in alternative embodiments, the handle portion 102 may include other means of allowing an individual to manipulated the apparatus. In particular, the finger loops 104, 106 could be replaced by any means that allow a user to translate the apparatus from a closed position (FIG. 1) to an open position (FIG. 2).

The finger loops 104, 106 are connected to a shaft 108. The shaft 108 connects the finger loops 104, 106 to grasping ends 110 and 112. In one embodiment, the shaft 108 is about 11 cm long and is about 0.4 cm wide.

Figure 2:
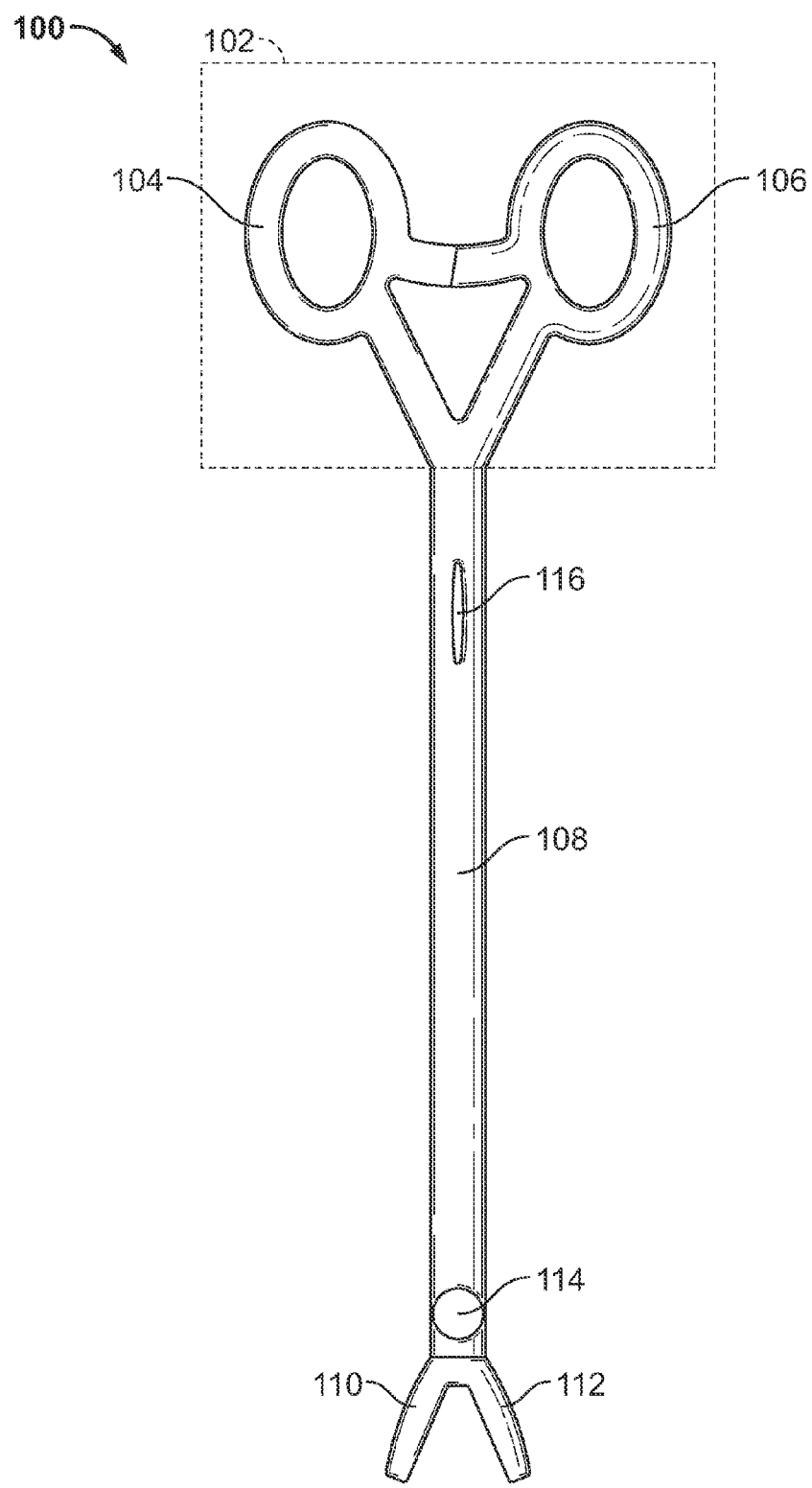
FIG. 2 shows a front plan view of an apparatus according to an embodiment of the present invention with the grasping ends in an open position.
Figure 3:
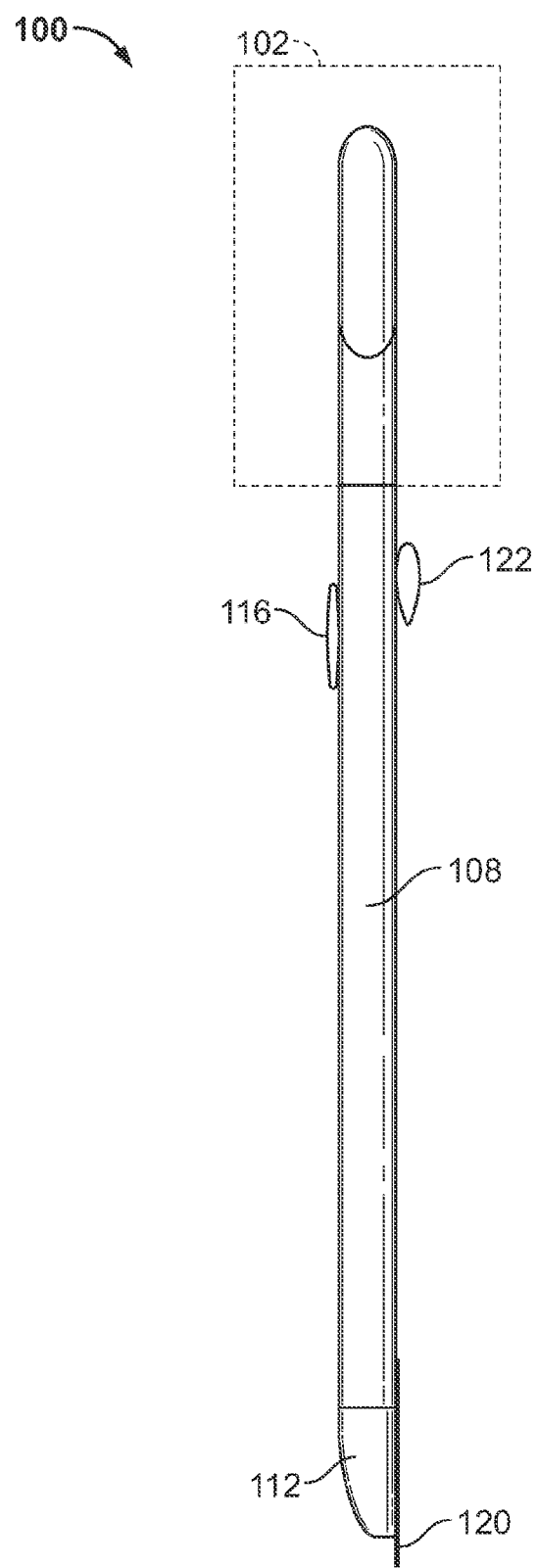
FIG. 3 shows a side view of an apparatus according to an embodiment of the present invention with a blade in an extended position.

The finger loops 104, 106 are moveable between a closed position (FIG. 1) and an open position (FIG. 2). In the closed position, grasping ends 110 and 112 are forced together and in the open position, the grasping ends 110 and 112 are separated from each other. In one embodiment, the grasping ends 110, 112 are at one end of the shaft 108 and the finger loops 104, 106 are at another. In the illustrated embodiment, the grasping ends 110, 112 open and close about a contact point 114. Of course, the grasping ends 110, 112 could open and close in other manners. For example, opening and closing of the finger loops 104, 106 could cause only one of the ends to move relative to the other to create a space there between.

In one embodiment, the grasping ends 110, 112 are formed by graduated stapling jaws to form a microstapler. That is, the grasping ends 110, 112 may be configured to deliver microstaples to the desired location that is pinched between them when they are in the closed position. To that end, the apparatus 100 may also include a stapler actuator 116 that causes the grasping ends 110, 112 to deliver a microstaple when pressed. In particular, pressing or otherwise activating stapler actuator 116 causes the grasping ends 110, 112 to deliver one or more microstaples to create a hemostatic staple line. In the case where the apparatus is used in a blood vessel harvesting procedure, the hemostatic staple line seals the vessel which can then be cut. In one embodiment, the staples are 1 cm double sided staples.

Figure 4:
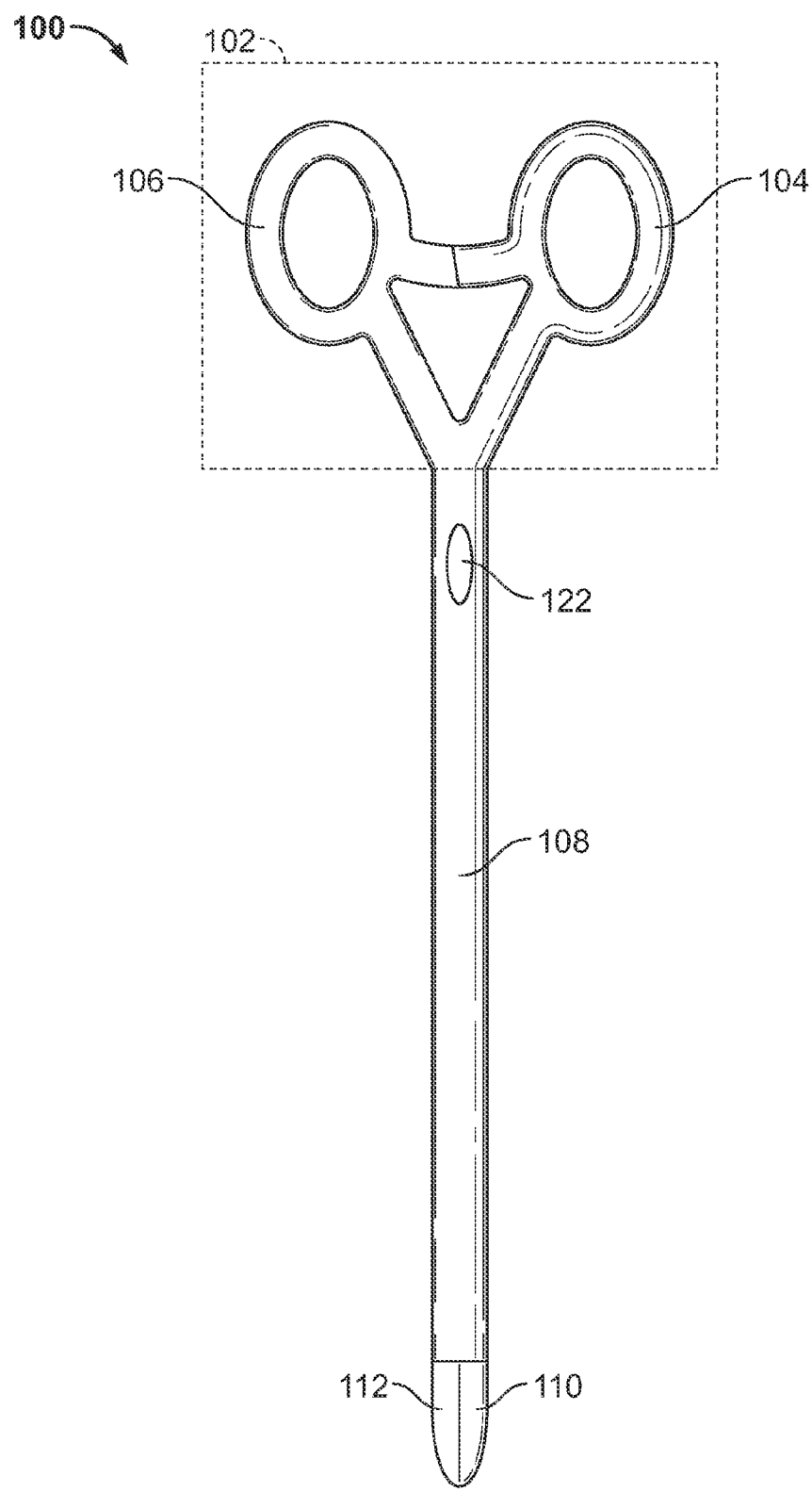
FIG. 4 shows a back plan view of an apparatus according to an embodiment of the present invention with the grasping ends in a closed position.

To assist in both delivering the grasping ends 110, 112 to an area of interest (e.g., to blood vessel to be harvested) and in cutting the area of interest, the apparatus may also include a blade 120. The blade 120 is housed within the shaft 108 in one embodiment. To control positioning of the blade 120, the apparatus 100 includes a blade actuator 122 that causes the blade 120 to translate from an extended position (FIG. 3) to a detracted position (FIGS. 1, 2 and 4). In one embodiment, the blade 120 is a #11 scalpel blade or the like.

In operation, the apparatus 100 is useful for removing an object from a being. In one embodiment, the apparatus 100 is useful to remove a blood vessel from a human. Of course, the blood vessel could be removed from an animal other than a human. The following discussion, however, relates to only humans for ease of description but is not so limited.

According to one embodiment, a starter incision may be made to the human in a region above or near the location of a blood vessel that is to be harvested. Of course, in one embodiment, the incision could be omitted. The apparatus 100 is then forced, in its closed position, through the skin and other tissue to the blood vessel. To aid in so forcing the apparatus 100, the blade 120 may be deployed such that it extends beyond a distal end of the grasping ends 110, 112 as shown, for example, in FIG. 4. The blade 120 may be retracted at any time. Of course, the blade 120 need not be deployed in while the apparatus 100 is forced below the skin.

When the blood vessel is located (typically with the aid of endoscope), the finger loops 104, 106 may be manipulated to cause the grasping ends 110, 112 to translate to the open position. In one embodiment, at this time the blade 120 should be in the retracted position to ensure the blood vessel is not inadvertently severed. Of course, this is not required.

The open grasping ends 110, 112 may then be closed about the blood vessel and the stapler actuator 114 manipulated to cause the grasping ends 110, 112 to deliver a line of one or more staples to seal the blood vessel. After the blood vessel is sealed, it may be cut by extending the blade 120. The grasping ends 110, 112 may the release the blood vessel and the apparatus 100 removed.

Utilizing the apparatus 100 in a manner as described above or similar thereto may provide many benefits over standard blood vessel harvesting techniques. For example, utilizing the apparatus 100 may allow for the maintenance of proper $CO_2$ insufflation of the blood vessel if an endoscope is being used. Further, because the blood vessel does not need to be pulled to the surface, the amount of intimal damage/hyperplasia may be reduced of eliminated. Further, deploying the staples as described above may minimize blood loss at the remaining stump.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. An apparatus comprising:
   grasping ends movable about a contact point between an open position to a closed position;
   a shaft coupled to the grasping ends;
   a handle coupled to the shaft that includes two or more elements that may be moved relative to one another and that cause the grasping ends to move from between the open and closed positions;
   a stapler actuator that causes a stapling mechanism within the grasping ends to deploy one or more staples;
   a blade coupled to the shaft; and
   a blade actuator that causes the blade to translate between extended and detracted positions, wherein in the extended position the blade extends distally beyond the contact point and in the retracted position the blade does not extend distally beyond the contact point;
   wherein in the extended position the blade extends distally beyond the grasping ends.

2. The apparatus of claim 1, wherein the stapler deploys the one or more staples in a single line.

3. An apparatus comprising:
   grasping ends movable about a contact point between an open position to a closed position;
   a shaft coupled to the grasping ends;
   a handle coupled to the shaft that includes two or more elements that may be moved relative to one another and that cause the grasping ends to move from between the open and closed positions;
   a blade coupled to the shaft; and
   a blade actuator that causes the blade to translate between extended and detracted positions, wherein in the extended position the blade extends distally beyond the grasping ends.

4. The apparatus of claim 3, further comprising:
   a stapler actuator that causes a stapling mechanism within the grasping ends to deploy single line of staples.

* * * * *